United States Patent
Furukawa et al.

(10) Patent No.: US 7,265,232 B2
(45) Date of Patent: Sep. 4, 2007

(54) PROCESS FOR PRODUCING GLYCIDYL ETHER

(75) Inventors: Yoshiro Furukawa, Osaka (JP); Yasushi Miki, Osaka (JP); Keisuke Yaegashi, Osaka (JP)

(73) Assignee: Daiso Co., Ltd., Osaka-Fu (JP)

( * ) Notice: Subject to any disclaimer, the term of this patent is extended or adjusted under 35 U.S.C. 154(b) by 0 days.

(21) Appl. No.: 10/515,384

(22) PCT Filed: May 29, 2003

(86) PCT No.: PCT/JP03/06731

§ 371 (c)(1),
(2), (4) Date: Nov. 23, 2004

(87) PCT Pub. No.: WO2004/002974

PCT Pub. Date: Jan. 8, 2004

(65) Prior Publication Data
US 2006/0030721 A1 Feb. 9, 2006

(30) Foreign Application Priority Data
May 30, 2002 (JP) ............................. 2002-157148

(51) Int. Cl.
C07D 301/28 (2006.01)
(52) U.S. Cl. .................................................. 549/517
(58) Field of Classification Search ................. 549/517
See application file for complete search history.

(56) References Cited

U.S. PATENT DOCUMENTS 5,130,314 A * 7/1992 Yasuda et al. ......... 514/252.04
5,130,482 A   7/1992 Takehira et al.

FOREIGN PATENT DOCUMENTS

JP  5-163260  6/1993
JP  6-37482   5/1994

OTHER PUBLICATIONS

McKillop et al, Tetrahedron, vol. 30, p. 1379-1382 (1974).*
V. I. Shvedov et al., "Synthesis and β-Adrenoblocking Properties of Certain Pindolol Analogs", Pharmaceutical Chemistry Journal, vol. 14, No. 11, pp. 794-798, Nov. 1980.
P. Camps et al.,"Stereoselective Syntheses of both Enantiomers of Ketoconazole from (R)- and (S)-Epichlorohydrin", Tetrahedron Asymmetry, vol. 6, No. 6, pp. 1283-1294, Jun. 1995.
V. Brizzi et al., "New 1,2,4-Oxadiazole Derivatives: Synthesis and Adrenergic Receptors Binding Studies", IL FARMACO, vol. 47, No. 6, pp. 953-966, Jun. 1992.

* cited by examiner

*Primary Examiner*—Bernard Dentz
(74) *Attorney, Agent, or Firm*—Wenderoth, Lind & Ponack, L.L.P.

(57) ABSTRACT

A process for producing a glycidyl ether and an optically active compound thereof with high yield and an optically high purity comprising reacting an alcohol with epihalohydrin in a base to thereby produce a glycidyl ether, the reaction performed in a two-layer system of a nonaqueous organic solvent and an aqueous solvent.

11 Claims, No Drawings

PROCESS FOR PRODUCING GLYCIDYL ETHER

This application is a U.S. national stage of International Application No. PCT/JP03/06731 filed May 29, 2003.

TECHNICAL FIELD

The present invention relates to a process for preparing glycidyl ethers and optically active compounds thereof which are important as intermediates for synthesizing medicines, agrochemicals and physiological active compounds.

BACKGROUND ART

Glycidyl ethers are important as intermediates for synthesizing a variety of medicines, and especially optically active glycidyl ethers have been recently utilized in development of the medicines.

It is generally required that optically active medicines or intermediates thereof are more than 98% in purity. Therefore, it is important problem to establish the process for preparing optically active glycidyl ethers in high purity.

As a general method for preparing racemic glycidyl ethers which are used for preparing a monomer of epoxide resin, the method which comprises reacting a mole of phenol with 3 to 7 moles of epichlorohydrin in an aqueous sodium hydroxide solution for several hours at 45 to 90° C. has been developed.

Furthermore, it is disclosed that an optically active glycidyl ether, which is an intermediate for preparing atenolol, represented by the following formula;

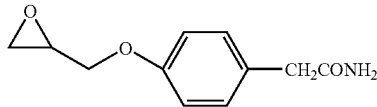

was prepared by reacting 4-carbamoylmethylphenol with an optically active epichlorohydrin in the presence of an alkali hydroxide and a quaternary ammonium salt in an aqueous solvent (Japanese Patent Publication B 6-37482).

However, the yield of glycidyl ethers and the optical purity of optically active compounds thereof were not satisfactory.

DISCLOSURE OF INVENTION

The present inventors have extensively studied in order to solve the above problem. As a result they have found that a glycidyl ether is obtainable in high yield and an optically active compound thereof is obtainable in high purity in case of preparing a glycidyl ether by reacting an alcohol with epihalohydrin in the presence of a base, wherein the reaction is carried out in a two-layer system of a nonaqueous organic solvent and an aqueous solvent, and have completed the present invention.

Namely, the present invention relates to a process for preparing a compound represented by the following formula (3);

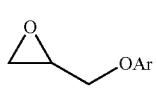

(3)

wherein Ar is substituted or unsubstituted aromatic group, which comprises reacting an alcohol represented by the following formula (1);

$$ArOH \tag{1}$$

wherein Ar is the same as defined above, in the presence of one mole or more than one mole of a base with one to three moles of epihalohydrin represented by the following formula (2);

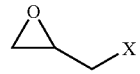

(2)

wherein X is halogen atom, in a two-layer system of a nonaqueous organic solvent and an aqueous solvent.

Furthermore, the present invention relates to a process for preparing glycidyl ether, which comprises carrying out the above reaction by adding a quaternary ammonium salt represented by the following formula (4);

$$R^1R^2R^3R^4N^+X^- \tag{4}$$

wherein $R^1$, $R^2$, $R^3$ and $R^4$ are the same or different, and are alkyl group, alkenyl group, aralkyl group or aryl group, and $X^-$ is chloride ion, bromide ion, iodide ion, hydrogensulfate ion or hydroxide ion.

According to the present invention, when epihalohydrin is used in an optically active form, an optically active glycidyl ether is obtainable in highly optical purity almost without its racemate.

The reaction principal of the present invention consist in that, when epihalohydrin which is nonaqueous and an alcohol presented in an aqueous basic solution are reacted, the concentration of epihalohydrin and the produced glycidyl ether which is nonaqueous decreases by adding a nonaqueous organic solvent. As a result, side-reaction by epihalohydrin and the glycidyl ether in a nonaqueous organic solvent and an alcohol in an aqueous basic solution is prevented, and thus the glycidyl ether is obtained in high yield and in high purity. Such a reaction principle in regard to the process for preparing a glycidyl ether starting from epihalohydrin has not been reported and is novel.

PREFERABLE MODE FOR CARRYING OUT THE INVENTION

The alcohol (1) used in this process includes an aromatic compound which is substituted by hydroxy group, such as unsubstituted phenol, or phenol having substituent(s).

The substituent is not limited as long as this reaction is effected, and there are illustrated saturated or unsaturated alkyl group, such as methyl, ethyl, allyl, etc., alkyl group having an ether-bond, such as methoxymethyl, 2-methoxyethyl, allyloxymethyl, (2-methoxyethoxy)methyl, (2-isopropoxyethoxy)methyl, etc., halogen atoms, such as fluoro, chloro, bromo or iodo atom, halogenoalkyl group, such as trifluoromethyl, chloromethyl, etc., alkoxy group, such as methoxy, allyloxy, methoxymethoxy, etc., amido group such as acetylamide, etc., carbamoylamide group, aldehyde group, acyl group, such as acetyl, benzoyl, etc., nitro group and so on, or the substituent may form a bridge, such as tetramethylene, methylenedioxy, etc. Furthermore, the above substituent may multiply present.

The above aromatic compound substituted by hydroxy group also includes a polycyclic aromatic compound substituted by hydroxy group, such as α-naphthol, β-naphthol, 7-hydroxyindene, etc., and further a heterocyclic aromatic compound, such as 2-pyridylalcohol, 3-hydroxyfuran, 4-hydroxyindole, 5-hydroxychinoline, etc.

Among the alcohols (1), phenols are preferable, especially unsubstituted phenol, 4-fluorophenol, 4-methylphenol, 4-methoxyphenol and 2-allyloxyphenol are preferable.

The bases used in this reaction include aqueous bases, such as an alkali hydroxide, e.g., lithium hydroxide, sodium hydroxide or potassium hydroxide, an alkali carbonate, e.g., sodium carbonate or potassium carbonate, potassium tert-butoxide, etc., but an alkali hydroxide is preferable, especially sodium hydroxide and potassium hydroxide are preferable.

The amount of the base used in this reaction is preferably one mole or more than one mole to an alcohol (1), more preferably 1~2 moles.

The epihalohydrin (2) used in this reaction includes epichlorohydrin, epibromohydrin and epiiodohydrin, preferably epichlorohydrin and epibromohydrin. The amount of the epihalohydrin is 1 to 3 moles to an alcohol (1), preferably 1.5~2 moles. The amount may be beyond 3 moles, but the yield is not necessarily increased. When the amount is less than one mole, an unreacted alcohol (1) and a reacted glycidyl ether (3) are further reacted and therefore, decrease of the purity and yield is caused.

The nonaqueous organic solvent used in this reaction is not limited as long as it does not mix and react with the aqueous basic solution, and dissolves epihalohydrin (2) and a glycidyl ether (3). It includes alkanes, such as hexane, heptane, etc., ethers, such as diethyl ether, dibutyl ether, tert-butylmethyl ether, etc., aromatic hydrocarbons, such as benzene, toluene, xylene, etc., halogenated compounds, such as chloroform, dichloromethane, 1,2-dichloroethane, etc., and preferably toluene, tert-butylmethyl ether and 1,2-dichloroethane.

The suitable amount of water used in this reaction is 1 to 20 times (w/w) to the amount of an alcohol (1). The amount of a nonaqueous organic solvent is 0.5~3 times (v/v) to the amount of water.

This reaction is promoted by adding a quaternary ammonium salt to give an objective glycidyl ether (1) in higher yield.

The quaternary ammonium salt (4) includes unlimitedly for example, benzyltrimethylammonium chloride, diallyldimethylammonium chloride, benzyltrimethyammonium bromide, n-octyltrimethylammonium bromide, stearyltrimethylammonium bromide, cetyldimethyethylammonium bromide, tetra n-butylammonium iodide, β-methylcholine iodide, tetra-n-butylammonium hydrogen sulfate, phenyltrimethylammonium hydroxide, etc.

The amount of a quaternary ammonium salt (4) used in this reaction is catalytic amount to an alcohol (1), preferably 0.005~0.1 mole.

The reaction temperature is preferably 0~50° C., more preferably 0~40° C. At less than 0° C. it is not preferable as the reaction is restrained and it is possible that water in the reaction medium is freezed. Furthermore, when the reaction temperature is beyond 50° C., it is not preferable, as side reaction progresses to cause decrease of yield, and further, when optically active epihalohydrin (2) is used, the racemization progresses and causes to decrease of the optical purity of an optically active glycidyl ether (1).

The merits of this reaction consist in that an objective glycidyl ether (3) is obtained in high yield and high purity by such a very simple procedure that after the reaction, the organic solvent is taken out and neutralized with a diluted mineral acid such as hydrochloric acid and then evaporate the solvent. Furthermore, when an optically active epihalohydrin (2) is used, optically active glycidyl ether (3) is obtained in the state almost keeping its optical purity. Especially when a reacted product, a glycidyl ether is liquid, the crystallization method is not available and therefore, by subjecting to the practice of the method of the present invention, the glycidyl ether can be at one time obtained in highly optical purity.

When the yield is low, after the reaction, sodium chloride, potassium chloride, sodium carbonate, potassium carbonate, magnesium sulfate or sodium sulfate is added in the suitable amount and then, the organic layer had better to be taken out and if necessary, the purification by distillation, crystallization or column chromatography may be carried out after evaporation of the organic solvent.

EXAMPLE

The present invention is explained by the following examples, but the present invention should not be limited by the examples.

Example 1

To a reaction vessel were added (R)-epichlorohydrin (99% ee, 60.0 g, 0.64 mol), benzyltrimethylammonium chloride (0.80 g), toluene (140 ml) and water (140 ml), and the mixture was cooled with ice. After adding 4-fluorophenol (48.5 g, 0.43 mol), thereto 24% aqueous NaOH solution (94.0 g, 0.56 mol) was dropped under stirring over a period of one hour. The mixture was stirred for 30 minutes under ice-cooling and then for 48 hours at room temperature. After the reaction the aqueous layer was removed and the organic layer was washed with 5% aqueous HCl solution (140 ml) and then water (70 ml). After removal of toluene, the residue was distilled to give objective (S)-glycidyl-4-fluorophenyl ether (61.5 g, yield 85%, optical purity 99% ee) as a colorless liquid.

bp 73-75° C./0.6-0.7 Torr

NMR (270 MHz, CDCl$_3$) σ 2.75 (1H, dd), 2.92 (1H, dd), 3.34 (1H, dddd), 3.90 (1H, dd), 4.20 (1H, dd), 6.77-7.02 (4H, m)

Example 2

To a reaction vessel were added (S)-epichlorohydrin (99% ee, 30.0 g, 0.32 mol), benzyltrimethylammonium chloride (0.80 g), toluene (70 ml) and water (70 ml), and the mixture was cooled with ice. After addition of phenol (20.3 g, 0.22 mol), thereto 24% aqueous NaOH solution (54.0 g, 0.33 mol) was dropped in a period of one hour under stirring. The mixture was stirred for 30 minutes under ice-cooling and then for 39 hours at room temperature. After the reaction the aqueous layer was removed and the organic layer was neutralized with 5% aqueous HCl solution (70 ml) and washed with water (40 ml). After removal of toluene, the residue was distilled to give objective (R)-glycidylphenyl ether (27.0 g, yield 83%, optical purity 98% ee) as a colorless liquid.

bp 85-86° C./0.8 Torr

NMR (270 MHz, CDCl$_3$) σ 2.76 (1H, dd), 2.91 (1H, dd), 3.36 (1H, dddd), 3.97 (1H, dd), 4.21 (1H, dd), 6.91-6.99 (3H, m), 7.25-7.32 (2H, m)

Example 3

To a reaction vessel were added (S)-epichlorohydrin (99% ee, 2.64 g, 29 mmol), toluene (6 ml) and water (6 ml), and the mixture was cooled with ice. After adding phenol (1.78 g, 19 mmol), thereto 24% aqueous NaOH solution (4.75 g, 29 mmol) was dropped under stirring over a ten minute period. The mixture was stirred for 30 minutes under ice-cooling and then for 50 hours at room temperature. The aqueous layer was removed and the organic layer was neutralized with 5% HCl and washed with water twice. The solvent was removed to give objective crude (R)-glycidylphenyl ether (1.96 g, yield 69%, optical purity 98% ee) as an oil.

Example 4

To a reaction vessel were added (S)-epichlorohydrin (99% ee, 2.64 g, 29 mmol), benzyltrimethylammonium chloride (36 mg), 1,2-dichloroethane (6 ml) and water (6 ml), and the mixture was cooled with ice. After addition of phenol (1.78 g, 19 mmol), thereto 24% aqueous NaOH solution (4.10 g, 25 mmol) was dropped in a ten minute period under stirring. The mixture was stirred for 30 minutes under ice-cooling and then for 42 hours at room temperature. After the aqueous layer was removed, the organic layer was neutralized with 5% HCl and washed with water twice. The solvent was removed to give objective crude (R)-glycidylphenyl ether (2.27 g, yield 80%, optical purity 98% ee) as an oil.

Example 5

To a reaction vessel were added (S)-epichlorohydrin (99% ee, 2.64 g, 29 mmol), benzyltrimethylammonium chloride (72 mg), tert-butylmethyl ether (6 ml) and water (6 ml), and the mixture was cooled with ice. After addition of phenol (1.78 g, 19 mmol), thereto 24% aqueous NaOH solution (4.75 g, 29 mmol) was dropped in a ten minute period under stirring. The mixture was stirred for 30 minutes under ice-cooling and then for 37 hours at room temperature. After the aqueous layer was removed, the organic layer was neutralized with 5% HCl and washed with water twice. The solvent was removed to give objective crude (R)-glycidylphenyl ether (2.13 g, yield 75%, optical purity 98% ee) as an oil.

Example 6

To a reaction vessel were added (R)-epichlorohydrin (99% ee, 5.00 g, 54 mmol), benzyltrimethylammonium chloride (50 mg), toluene (45 ml) and water (45 ml), and the mixture was cooled with ice. After addition of p-cresol (2.92 g, 27 mmol), thereto 24% aqueous NaOH solution (6.75 g, 40 mmol) was dropped in a ten minute period under stirring. The mixture was stirred for 30 minutes under ice-cooling and then for 30 hours at 45° C. After the reaction mixture was cooled at room temperature, the organic layer was taken out and washed with 5% aqueous HCl solution (30 ml) and then with water (30 ml) twice. Toluene was removed to give objective crude (S)-glycidy-4-methylphenyl ether (3.58 g, yield 81%, optical purity 98% ee) as an oil.

NMR (270 MHz, CDCl$_3$) σ 2.45 (3H, S), 2.76 (1H, dd), 2.91 (1H, dd), 3.37 (1H, dddd), 3.83 (1H, dd), 4.17 (1H, dd), 6.57-7.12 (4H, m)

Example 7

To a reaction vessel were added (R)-epichlorohydrin (98% ee, 7.40 g, 54 mmol), benzyltrimethylammonium chloride (0.54 g), toluene (15 ml) and water (15 ml), and the mixture was cooled with ice. After addition of 4-methoxyphenol (6.70 g, 27 mmol), thereto 24% aqueous NaOH solution (6.75 g, 40 mmol) was dropped in a ten minute period under stirring. The mixture was stirred for 30 minutes under ice-cooling and then for 35 hours at room temperature. After the aqueous layer was removed, the organic layer was taken out and washed with 5% aqueous HCl solution (15 ml) and then with water (15 ml) twice. Toluene was removed to give objective crude (S)-glycidy-4-methoxyphenyl ether (4.33 g, yield 89%, optical purity 98% ee) as an oil.

NMR (270 MHz, CDCl$_3$) σ 2.75 (1H, dd), 2.90 (1H, dd), 3.37 (1H, dddd), 3.84 (1H, dd), 3.95 (3H, S), 4.19 (1H, dd), 6.61-6.93 (4H, m)

Example 8

To a reaction vessel were added (R)-epichlorohydrin (99% ee, 3.00 g, 32 mmol), benzyltrimethylammonium chloride (40 mg), 2-allyloxyphenol (3.24 g), toluene (7.2 ml) and water (7.2 ml), and the mixture was cooled with ice. Thereto 24% aqueous NaOH solution (5.40 g, 32 mmol) was dropped in a 15 minute period under stirring. The mixture was stirred for 30 minutes under ice-cooling and then for 48 hours at room temperature. After the reaction the aqueous layer was removed and the organic layer was taken out and washed with 5% aqueous HCl solution (10 ml) and then with water (10 ml). Toluene was removed to give objective crude (S)-allylglycidy ether (3.79 g, yield 86%, optical purity 98% ee) as an oil.

NMR (270 MHz, CDCl$_3$) σ 2.76 (1H, dd), 2.89 (1H, dd), 3.36-3.40 (1H, m), 4.04 (1H, dd), 4.25 (1H, dd), 4.57-4.61 (2H, m), 5.25-5.30 (1H, m), 5.37-5.45 (1H, m), 6.01-6.13 (1H, m), 6.88-96 (4H, m)

Comparative Example 1

To a reaction vessel were added (R)-epichlorohydrin (99% ee, 1.00 g, 11 mmol), 4-fluorophenol (1.21 g, 11 mmol), benzyltrimethylammonium chloride (10 mg) and water (3.6 ml), and the mixture was cooled with ice. Thereto 24% aqueous NaOH solution (2.16 g, 13 mmol) was dropped in a 10 minute period under stirring. The mixture was stirred for 1 hour under ice-cooling and then for 28 hours at room temperature. After the reaction the reaction mixture was extracted with toluene (3.6 ml) and the extract was separated with a separating funnel. The organic layer was washed with 5% aqueous HCl solution and then with water twice. The solvent was removed to give objective crude (S)-glycidy-4-fluorophenyl ether (0.98 g, yield 54%, optical purity 95% ee) as an oil.

Comparative Example 2

To a reaction vessel were added (S)-epichlorohydrin (99% ee, 2.64 g, 29 mmol), methanol (9 ml) and water (6 ml), and the mixture was cooled with ice. After phenol (1.79 g, 19 mmol) was added, thereto 24% aqueous NaOH solution (4.10 g, 25 mmol) was dropped in a 10 minute period under stirring. The mixture was stirred for 30 minutes under ice-cooling and then for 37 hours at room temperature. After removal of methanol, the reaction mixture was extracted with toluene (3.6 ml). The organic layer was neutralized with 5% HCl and washed with water twice. The solvent was removed to give crude (R)-glycidyphenyl ether (1.49 g, yield 52%, optical purity 92% ee) as an oil.

Comparative Example 3

To a reaction vessel were added (S)-epichlorohydrin (99% ee, 2.64 g, 29 mmol), tetrahydrofuran (9 ml), benzyltrimethylammonium chloride (36 mg) and water (6 ml), and the mixture was cooled with ice. After phenol (1.79 g, 19 mmol) was added, thereto 24% aqueous NaOH solution (4.75 g, 29 mmol) was dropped in a 10 minute period under stirring. The mixture was stirred for 30 minute under ice-cooling and then for 41 hours at room temperature. After removal of tetrahydrofuran, the reaction mixture was extracted with toluene. The organic layer was neutralized 5% HCl and washed with water twice. The solvent was removed to give crude (R)-glycidyphenyl ether (1.08 g, yield 38%, optical purity 92% ee) as an oil.

INDUSTRIAL APPLICABILITY

According to the method of the present invention, by such a very simple procedure that after the reaction the organic solvent is taken out and was neutralized with a diluted mineral acid such as diluted hydrochloric acid and the organic solvent is removed, there was obtained a glycidyl ether represented by the formula (3) in high yield and high purity and an optically active compound thereof in optically high purity.

The invention claimed is:

1. A process for preparing a glycidyl ether represented by the following formula (3);

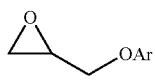 (3)

wherein Ar is unsubstituted phenyl, phenyl substituted by saturated or unsaturated alkyl, phenyl substituted by alkoxy, or phenyl substituted by halogen, 1-naphthyl or 2-naphthyl, which comprises reacting an alcohol represented by the following formula (1);

ArOH (1)

wherein Ar is the same as defined above, at 0 to 50° C. in the presence of one mole or more than one mole of a base, and a quaternary ammonium salt represented by the following formula (4);

 (4)

wherein $R^1$, $R^2$, $R^3$ and $R^4$ are the same or different, and are alkyl group, alkenyl group, aralkyl group or aryl group, and X- is chloride ion, bromide ion, iodide ion, hydrogensulfate ion or hydroxide ion, and with one to three moles of epihalohydrin represented by the following formula (2);

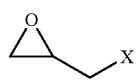 (2)

wherein X is halogen atom, in a two-layer system of a nonaqueous organic solvent selected from the group consisting of toluene, tert-butylmethyl ether and 1,2-dichloroethane, and an aqueous solvent.

2. The process for preparing glycidyl ether according to claim 1 wherein the epihalohydrin is epichlorohydrin or epibromohydrin.

3. The process for preparing glycidyl ether according to claim 1 wherein the base is an alkali hydroxide.

4. The process for preparing glycidyl ether according to claim 1 wherein the alcohol is unsubstituted phenol, cresol, methoxyphenol, allyloxyphenol or phenol substituted by halogen.

5. The process for preparing glycidyl ether according to claim 4 wherein the alcohol is phenol, 4-fluorophenol, 4-methylphenol, 4-methoxyphenol or 2-allyloxyphenol.

6. The process for preparing optically active glycidyl ether according to claim 1 wherein the epihalohydrin is an optically active compound.

7. The process for preparing glycidyl ether according to claim 2 wherein the base is an alkali hydroxide.

8. The process for preparing glycidyl ether according to claim 2 wherein the alcohol is unsubstituted phenol, cresol, methoxyphenol, allyloxyphenol or phenol substituted by halogen.

9. The process for preparing glycidyl ether according to claim 3 wherein the alcohol is unsubstituted phenol, cresol, methoxyphenol, allyloxyphenol or phenol substituted by halogen.

10. The process for preparing glycidyl ether according to claim 8 wherein the alcohol is phenol, 4-fluorophenol, 4-methylphenol, 4-methoxyphenol or 2-allyloxyphenol.

11. The process for preparing glycidyl ether according to claim 9 wherein the alcohol is phenol, 4-fluorophenol, 4-methylphenol, 4-methoxyphenol or 2-allyloxyphenol.

* * * * *